United States Patent [19] [11] 4,185,621
Morrow [45] Jan. 29, 1980

[54] BODY PARAMETER DISPLAY INCORPORATING A BATTERY CHARGER

[75] Inventor: Richard B. A. Morrow, Corpus Christi, Tex.

[73] Assignee: Triad, Inc., Robstown, Tex.

[21] Appl. No.: 846,562

[22] Filed: Oct. 28, 1977

[51] Int. Cl.² .............................................. A61B 5/02
[52] U.S. Cl. .................................... 128/672; 128/670; 128/690; 128/736; 310/319; 310/339
[58] Field of Search ...................... 128/2.05 P, 2.05 T, 128/2.05 E, 2.05 A, 2.05 R, 2.06 F, 2 H; 310/319, 339

[56] References Cited

U.S. PATENT DOCUMENTS

| | | | |
|---|---|---|---|
| 2,658,505 | 11/1953 | Sheer | 128/2.05 P |
| 2,702,354 | 2/1955 | Chorpening | 128/2.05 P X |
| 2,756,741 | 7/1956 | Campanella | 128/2.05 T |
| 2,815,748 | 12/1957 | Boncke | 128/2.05 T |
| 3,405,288 | 10/1968 | Dittrich | 128/2.05 P X |
| 3,714,939 | 2/1973 | Day et al. | 128/2.05 A |
| 3,807,388 | 4/1974 | Orr et al. | 128/2.05 P X |
| 3,841,314 | 10/1974 | Page | 128/2.05 P |
| 3,871,362 | 3/1975 | Dunegan | 128/2.05 P X |
| 3,978,849 | 9/1976 | Geneen | 128/2.05 T |
| 3,996,926 | 12/1976 | Birnbaum | 128/2.05 A |

Primary Examiner—Lee S. Cohen
Attorney, Agent, or Firm—G. Turner Moller

[57] ABSTRACT

There is disclosed a body parameter display device incorporated in a digital wrist watch for alternatively displaying time and a value representative of the body parameter. A pressure sensor incorporated in the device delivers an electrical output which is manipulated to deliver a signal proportional to the blood pressure sensing. In addition, the electrical pulses are manipulated to deliver a value representative of pulse rate. The pressure sensor also delivers an electrical output which is used to energize the watch and display mechanism and/or to charge a battery contained in the watch casing.

9 Claims, 7 Drawing Figures

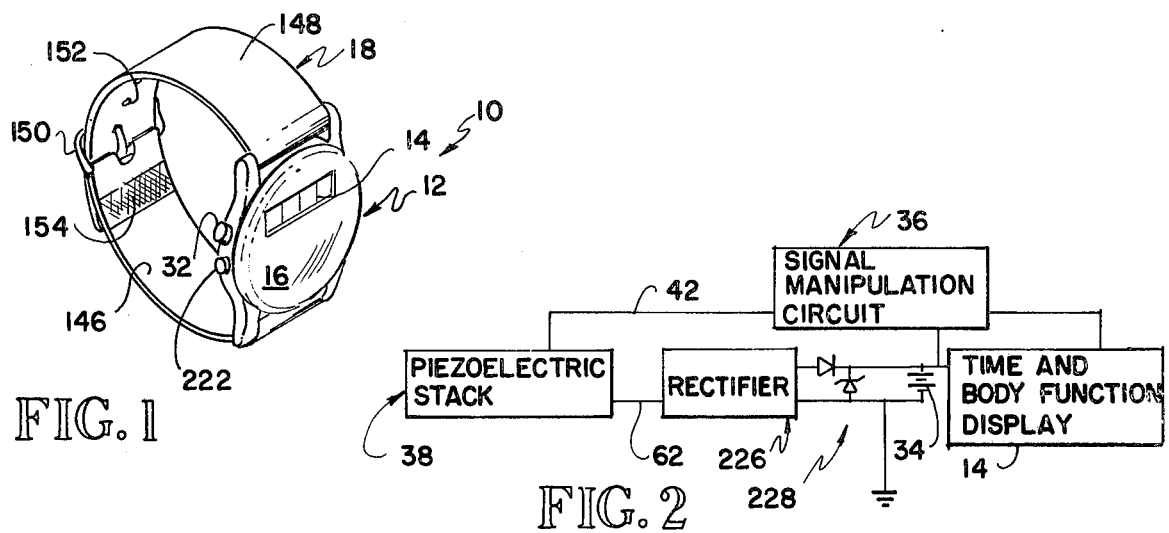
FIG. 1
FIG. 2
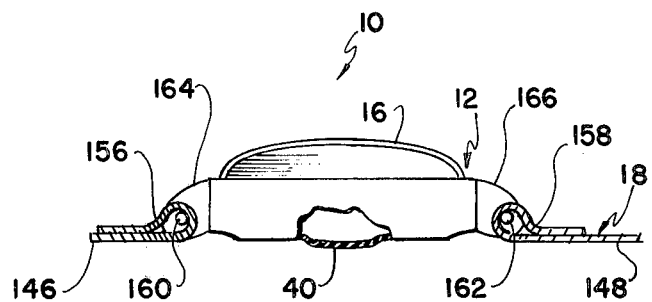
FIG. 7
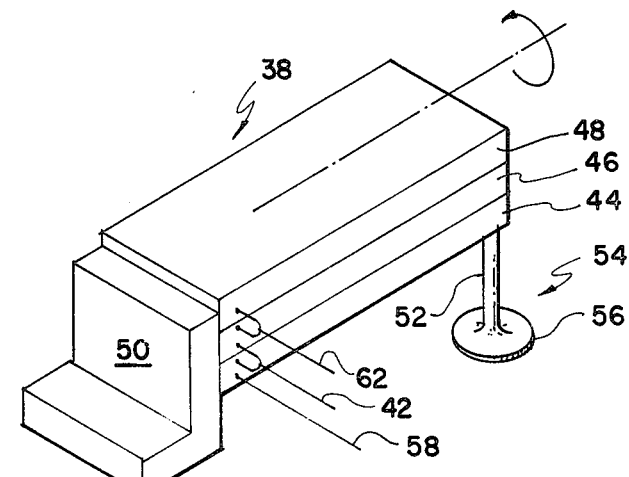
FIG. 4

BODY PARAMETER DISPLAY INCORPORATING A BATTERY CHARGER

This application is an improvement over the disclosure in Application Ser. No. 755,018 filed Dec. 28, 1976, now abandoned.

This invention relates to body parameter display devices and particularly to blood pressure and pulse rate indicating devices which are habitually worn by the user in the form of a wrist watch.

There are a substantial number of people who are afflicted with cardiac or cardiovascular difficulties which necessitate, or render desirable, periodic monitoring of blood pressure and/or pulse rate. Although pulse rate is capable of being read with a minimum of auxillary equipment, the current commercially available technique for reading blood pressure is the cuff device which not only requires a modicum of expertise to operate but which is also bulky and not apt to be habitually carried. It will be evident that it would be highly advantageous to provide a small blood pressure monitor that can be habitually worn by an individual without the least discomfort.

The provision of a wrist worn blood pressure and pulse rate indicator is known in the prior art as shown in U.S. Pat. No. 3,535,067. It will be apparent that this particular device is comprised of a multiplicity of mechnaical parts which, by the nature thereof, are necessarily intricate, expensive and prone to failure. Another wrist worn blood pressure and pulse rate indicator is known in the prior art as shown in U.S. Pat. No. 2,756,741. This devices uses antiquated vacuum tube components and contains a number of disadvantages, among which is that it is incapable of being habitually worn.

Also known in the prior art are wrist worn electric pulse rate display devices as shown in U.S. Pat. Nos. 3,742,937; 3,807,388; and 3,838,684. Of similar import is the disclosure in U.S. Pat. No. 3,426,747. Other body parameter display devices of more general interest are found in U.S. Pat. Nos. 2,815,748; 3,714,939; and 3,871,362; and 3,996,926. Of more general interest is the disclosure in U.S. Pat. No. 3,803,834.

One of the difficulties with habitually worn wrist carried electronic devices is that the batteries used as a power supply have a moderate expected life. When utilizing a habitually worn electronic device to indicate such body parameters as blood pressure and pulse rate, it is highly desirable that the expected battery life be extended as long as possible.

The provision of piezoelectric devices that are mechanically distorted to provide an electrical output used as a power source are known in the prior art, such as shown in Biomedical Engineering Systems, pages 394–397 and Transactions of the American Society for Artificial Internal Organs, Volume 9, 1963, pages 174–177. Devices incorporating series connected piezoelectric elements or delivering relatively high voltages are found in U.S. Pat. Nos. 3,395,295; 3,397,328; and 3,590,287. Of more general interest are the disclosures in U.S. Pat. No. 3,707,636 and Japan patent 46-30872.

The body parameter display device of this invention comprises a habitually worn wrist watch having a casing incorporating a pressure sensor biased against the wrist of the wearer. The pressure sensor delivers a first electrical output which is electronically manipulated to deliver an electrical signal of a value representative of the blood pressure of the wearer. In addition, the first electrical output may be electronically converted to deliver a signal representative of the pulse rate of the user. The blood pressure and/or pulse signals are displayed on a digital display array carried by the watch casing.

The pressure sensor delivers a second electrical output which is manipulated to provide a power source for operating the electronic components of the device and/or to charge a battery used to energize the watch.

It is an object of this invention to provide a compact, inexpensive wrist worn device having an extended battery life.

Another object of this invention is to provide a blood pressure display device incorporating a pressure sensor which delivers an electrical output that is manipulated to deliver a signal representative of a body parameter and an electrical output which is used to energize the device and to charge a battery thereof.

A further object of the invention is to provide a body worn blood pressure display device incorporating a sensor for delivering sequential electrical signals representative of sequential blood pressure pulses, a peak detector for analyzing each signal for detecting the maximum peak in each signal and delivering a value representative thereof and means for storing the signal representative of the maximum peak and means for displaying the maximum peak signal.

Other objects and a fuller understanding of the invention may be had by referring to the following description and claims taken in conjunction with the accompanying drawings.

IN THE DRAWINGS

FIG. 1 is an isometric view of a body parameter display device in accordance with the principles of this invention;

FIG. 2 is a simplified block diagram of the circuitry in the device of FIG. 1;

FIG. 4 is an isometric view of one form of sensor useable in the device of this invention;

FIG. 7 is a partial longitudinal cross-sectional view of the assembled watch casing and band.

Figure 5:
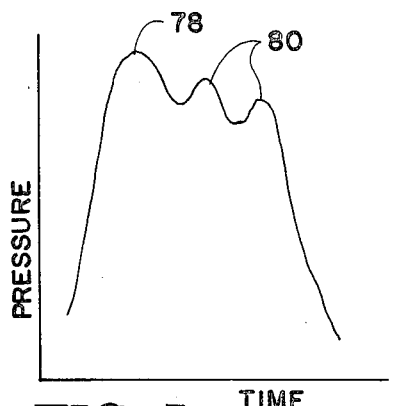
FIG. 5 is a graph representative of the pressure pulses occuring in a single heartbeat.

Referring to FIG. 1, there is illustrated a body parameter display device 10 embodied in a wrist watch comprising a casing 12 having a single digital display array 14 visible through a conventional watch crystal 16 and providing a band 18 for mounting the watch casing on an individual's wrist in a conventional manner.

Figure 3:
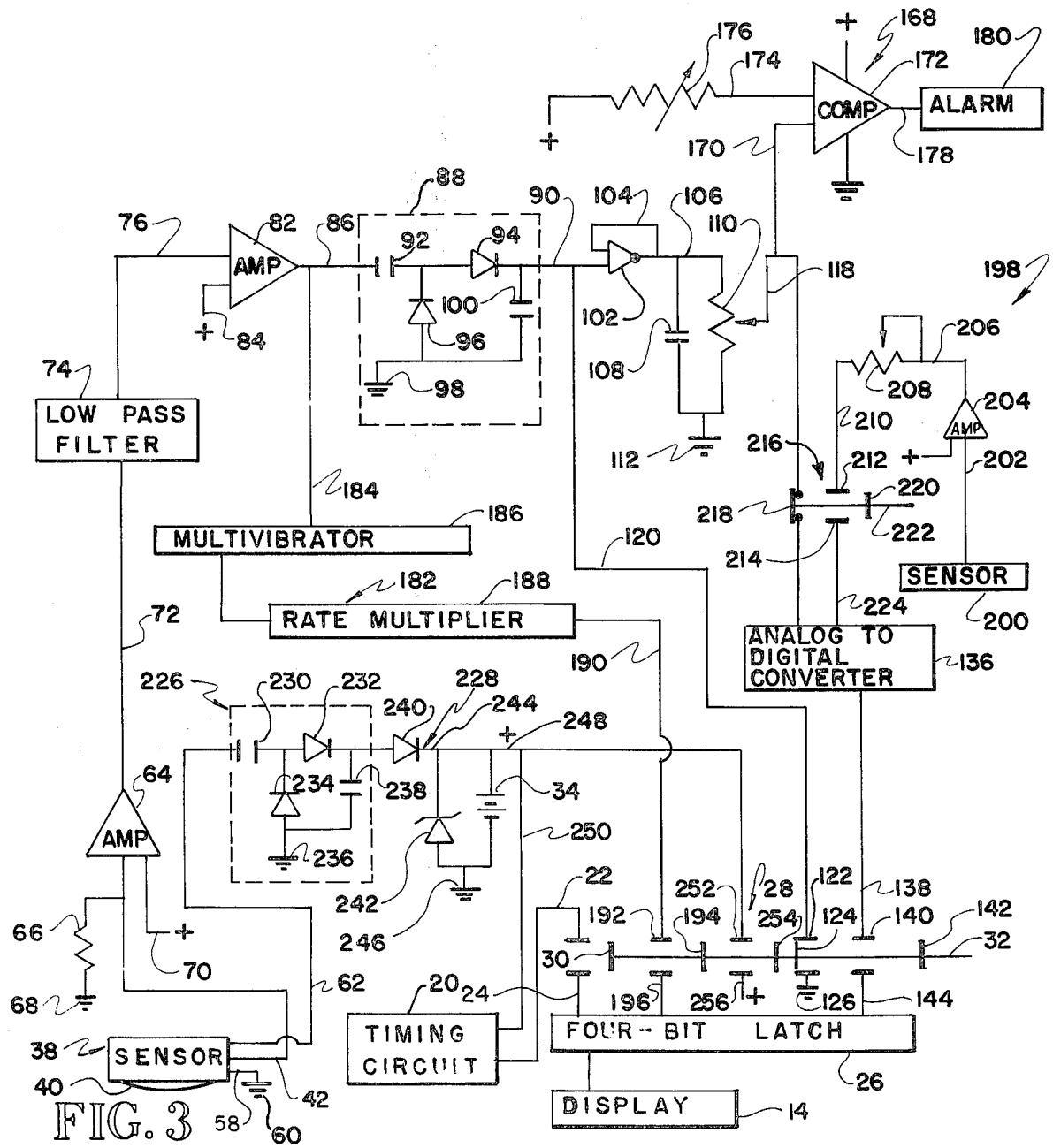
FIG. 3 is a more complete block diagram of the circuitry of FIG. 2.

Referring to FIGS. 2 and 3, there is housed inside the casing 12 a timing circuit 20 having an output 22 connected to the display array 14 through a lead 24, a conventional four bit latch 26 and a switch 28. The switch 28 may be of any suitable type, for example, comprising a switch element 30 and a switch actuator 32 extending out of the casing 12 arranged to connect the timing circuit 20 to the display array 14 for indicating time on the array 14 in a conventional manner. As will become more fully apparent hereinafter, the purpose of the switch 28 is not necessarily to isolate the display 14 from a power source or battery 34 to prolong the life thereof but is instead to alternatively connect the single array 14 to a circuit 36 for displaying a value representative of a body parameter on the array 14.

It is accordingly evident that the switch element 30 may be in a normally open position as illustrated in FIG. 3 thereby requiring depression of the switch actuator 32 to display time or may be in a normally closed position to continuously display time on the array 14. In the embodiment of FIG. 3, the user must push on the actuator 32 to indicate time and to display a body parameter measurement. It will accordingly be evident that the display 14 may include light emitting diodes, liquid crystals or any other suitable indicating components.

The circuit 36 comprises a sensor 38 for converting pressure pulses applied to a diaphragm or encapsulated feeler 40 into electrical signals on an output 42 representative of the magnitude of the pressure pulses sensed by the diaphragm 40. As shown best in FIG. 4, the sensor 38 is preferably a stack of piezoelectric crystals or wafers 44, 46, 48 which are separated by insulating layers and bonded together. The wafers 44, 46, 48 are mounted, at one end thereof, by a bracket 50 to the watch casing 12. Mounted on the other end of the wafers 44, 46, 48, offset from the axis thereof, is a stem 52 of a pressure foot 54 having an enlarged head 56 extending through an opening (not shown) in the watch casing 12. the head 56 engages the diaphragm 40 which acts to seal the watch casing 12 against the entry of moisture, dust and the like.

As best visualized by comparison of FIGS. 3 and 4, a lead 58 extends from one of the piezoelectric wafers through a ground connection 60 and affords a reference for the remaining leads 42, 62 of the pressure sensor 38. It will be evident that distortion of the piezoelectric wafers 44, 46, 48 in response to the pressure pulses of the wearer creates electrical signals in the outputs 42, 62.

The output 42 of the sensor 38 is connected to an amplifier 64 and a resistor 66 connected to a ground 68. The amplifier 64 also includes a power input 70 and an output 72. The amplifier 64 desirably comprises a four stage operational amplifier available from National Semiconductor as a Model LM324. This type amplifier incorporates four independent operational amplifiers in one component and is capable of operation from a single voltage supply. Because only one amplifier is used as the amplifier 64, the other amplifiers are available for use in succeeding stages of the circuit 36.

The output 72 of the amplifier 64 is connected to a low pass filter 74 which passes electrical signals of a frequency between direct current and 5 cycles per second and rejects electrical signals having a frequency higher than 8 cycles per second by a minimum of thirty decibels per octave. These requirement can be met with a conventional sixth order active filter comprising the three unused operational amplifiers on the four stage amplifier LM324 wired as illustrated in Active Filter Cookbook, by Don Lancester, 1975, page 144. The signals appearing on an output 76 of the filter 74 in the range of 6–7 cycles per second will be substantially attenuated as will be apparent to those skilled in the art. A compact amplifier/low pass filter is accordingly provided.

By using a very low frequency filter, only the very low frequencies representative of pulse beats are allowed to pass into the output 76 of the filter 74. Accordingly, all other frequencies are eliminated thereby creating a rather clean signal on the output 76 from a somewhat noise signal on the amplifier output 72.

One of the problems associated with the design of blood pressure display devices using a sensor delivering an electrical output signal is that the pressure input sensor is not a simple pressure spike. More typically, the pressure sensed during a single heartbeat is as illustrated in FIG. 5 where the pressure peak 78 is caused directly by heart muscle contraction whereas the secondary peak 80 or peaks are caused by contraction and relaxation of arteries through which blood moves. The magnitude of the secondary peaks 80 varies widely from individual-to-individual. Thus, the secondary peaks 80 comprise noise or irrelevant data.

The filter output 76 is connected to a second amplifier 82 of any suitable type having a power input 84 and an output 86 connected to a peak detecting circuit 88. The peak detecting circuit 88 acts to detect only the maximum peak 78 of the each pulse passed through the output 76, to convert the peak 78 to a direct current voltage value representative of the maximum value of each pulse peak 78 and to deliver the direct current voltage to an output 90. The peak detecting circuit 88 may be of any suitable type and conveniently comprises a capacitor 92 in series with a diode 94, a second oppositely facing diode 96 connected at one end between the capacitor 92 and the diode 94 and connected at the other end to a ground connection 98, and a capacitor 100 connected at one end to the output end of the diode 94 and connected at the other end to the ground connection 98.

Figure 6:
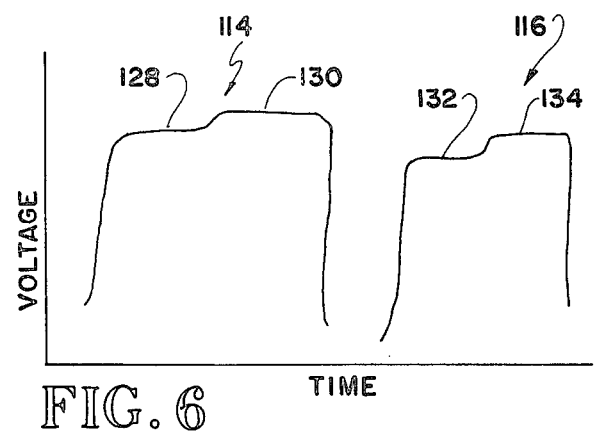
FIG. 6 is a graph representative of the output of the circuitry of FIG. 3 over two successive operations thereof.

Connected to the output 90 is an amplifier 102 wired as a voltage follower by having a lead 104 connecting the output 106 of the amplifier 102 to one of its input terminals. The voltage following amplifier 102 acts to maintain a voltage in a capacitor 108 that is identical with the highest voltage appearing in the capacitor 100 during any series of pulses delivered on the output 90 of the peak detecting circuit 88. The capacitor 108 is connected in parallel with a potentiometer 110 and both are connected to a ground connection 112. The potentiometer 110 acts as a calibrating device to display on the array 14 a value which corresponds with the individual's blood pressure as measured by an alternative and more direct mechanism, for example a cuff. Referring to FIG. 6, there are shown a pair of response curves 114, 116 indicating the voltage appearing in the output 118 of the potentiometer 110. The curves 114, 116 are generated during successive depressions of the switch actuator 32 as allowed by a lead 120, switch terminal 122 and switch element 124 on the actuator 32 arranged to momentarily contact the terminal 122 during switch actuation. When the actuator 32 is depressed to read out a blood pressure value, the switch element 124 moves into contact with the terminal 122 thereby discharging the capacitor 100 to a ground 126 and then moves out of contact with the terminal 122 thereby allowing the capacitor 100 to hold a charge. When the switch actuator 32 is released, the switch element 124 momentarily moves into contact with the switch terminal 122 thereby grounding the capacitor 100 and then moves out of contact therewith. The momentary discharge of the capacitor 100 allows a fresh pressure sensing to be read.

During generation of the curve 114, the voltage rises to a value 128 corresponding to the highest voltage value appearing in the capacitor 100 until a higher voltage value appears in the capacitor 100 which is reflected in a voltage value 130 in the potentiometer output 118. When the switch actuator 32 is disconnected from the potentiometer output 118, the voltage leaks off of the capacitor 100 to the ground 112. Upon the next depression of the switch actuator 32, the voltage curve 116 is generated and exhibits a voltage value 132 corresponding to the voltage appearing in the capacitor 100 until a higher value appears in the capacitor 100 which is reflected as a voltage value 134.

Although a resistor of fixed value may be used in lieu of the potentiometer 110, the latter is preferred because it allows calibration or adjustment of the circuit 36 in much the same manner as adjusting the gain of the amplifiers 64, 82 would act to calibrate the circuit 36. As will be more fully apparent hereinafter, the mechanical aspects of the display device 10 introduce a number of variables unrelated to blood pressure of the user which can affect the values displayed on the array 14. By providing the potentiometer 118, these mechanical variables can be adjusted out of the system.

The potentiometer output 118 is connected to an analog-to-digital converter 136 where the analog voltage signal present on the output 118 is converted to a digital signal on the lead 138. The converter 136 may be of any suitable type such as is available from Motorola Semiconductor as MC14433. All such converters operate to deliver a digital signal on the output 138 corresponding to the voltage level on the output 118. The converter 136 accordingly converts the signal on the output 118 into a signal which is compatible with the display array 14.

The converter output 138 is connected to a terminal 140 adjacent a switch element 142 on the actuator 32 which acts to connect the output 138 to a lead 144 operatively connected to the four bit latch 26 and the array 14. It will accordingly be seen that manipulation of the actuator 32 acts selectively to display either a value representative of time or a value representative of blood pressure on the array 14.

Referring to FIGS. 1 and 7, the watch band 18 is shown as comprising a pair of wrist encircling straps 146, 148 respectively providing a buckle 150 and a plurality of openings 152. The strap 146 preferably provides an elastic section 154 therein for purposes more fully explained hereinafter. The straps 146, 148 provide a pair of spaced watch attaching devices 156, 158 of any suitable type which are illustrated as loops for securement to a pin connection 160, 162 provided in a pair of ears 164, 166 comprising part of the watch casing 12 as shown in FIG. 7.

Referring to FIG. 7, the diaphragm 40 of the sensor 38 projects below the bottom of the watch casing 12 and is in pressure transmitting relation with the enlarged pad 56 of the pressure foot 54. The diaphragm 40 need extend only a very small distance below the watch casing 12, for example one millimeter.

One of the difficulties of blood pressure display devices which are designed to be habitually worn by the user is to provide consistent and reliable readings on the array 14. There are a number of problems including the establishment of consistent and reliable pressures between the diaphragm 40 and the arm of the user, the establishment of consistent and reliable pressures between the diaphragm 40 and the pressure foot 50 and calibration of the circuit 36. It will be evident that if the straps 146, 148 are bound very tightly to the user's wrist, the readings on the array 14 may be significantly different than when the straps 146, 148 are still snug but substantially looser. This variable is obviated to a significant extent by the elastic portion 154 which acts to maintain a more-or-less consistent hoop stress on the band 18. The attachment between the watch casing 12 and the straps 146, 148 may, due to manufacturing tolerances, constitute a variable which tends to change the readings on the array 14 independently of the user's blood pressure. It is evident that these problems are one-time or fitting problems to assure that the device 10 is suited for use by a particular person.

In one respect, it is not essential that the array 14 display values which are substantially accurate. This occurs when the user has been made aware of what his blood pressure actually is, as measured by more conventional equipment, concurrently with the readings on the array 14. By simple comparison, the user will be aware that so long as the readings on the array 14 remain the same, there is no substantial change in blood pressure. This is, of course, somewhat less than desirable.

Although it is possible to correct these fitting problems mechanically, as by adjusting the watch band 18 or by adjusting the mounting between the casing 12 and the straps 146, 148, it is preferred to effect this adjustment electrically in the circuit 36 by the adjustment of the potentiometer 110 or by the provision of means for adjusting the gain in the amplifiers 64, 82. Accordingly, when the device 10 is first fitted on the wearer, a blood pressure reading is taken by a more conventional device and the potentiometer 110 is adjusted until the readings displayed on the array 14 correspond thereto. In addition to the elastic portion 154 and the calibration of the circuit 36, there may also be provided a switch having a pressure foot extending out of the casing 12 and biased into engagement with the user's wrist. This switch is in circuit with the battery 34, for example, to prevent illumination of the array 14 until a predetermined force depresses the foot and closes the switch. Thus, there may be assurance that the straps 146, 148 are at least minimally snug on the user's wrist.

Another problem in assuring consistent and reliable readings on the array 14 occurs because of slow changes in the user or in the device 10 which are not related to pressure pulses applied to the sensor 38. If the user gains or looses a substantial amount of weight or if the watch mounting becomes loose in use, a change in the pressure contact between the user's arm and the diaphragm 40 will occur thereby affecting the readings on the array 14. These changes can be readily accomodated by periodic blood pressure checks by the user's physician followed by recalibration of the circuit 36 by manipulating the calibration means or potentiometer 110.

Referring back to FIG. 3, there is illustrated an alarm circuit 168 which may be incorporated in the circuit 36 by a lead 170 connected to the output 118 of the potentiometer 110. Connected to the lead 170 is a comparator 172, such as an operational amplifier available from National Semiconductor as Model LM339, having an input 174. The quantity of the signal on the input 174 is adjustable by the provision of a potentiometer or adjustable resistance 176 connected with the battery 34. When the quantity of the signal on the input 174 equals the quantity of the signal on the output 118, a circuit is completed through the comparator 172 and its output 178 to energize an alarm transducer 180 thereby signalling the user that his current blood pressure exceeds the limit value set into the input 174. The alarm transducer 180 may be of any suitable type and may be either of the audible or tactile variety. One suitable type alarm transducer is found in a watch made by Citizens Quartz. It is evident that the quantity of the signal on the input 174 is adjustable to accomodate a wide range of high blood pressure readings which will trip the alarm 180.

In the alternative, the comparator 172 may be an operational amplifier which is arranged to trigger the alarm 180 when the quantity of the signal on the lead 170 falls below the quantity of the signal on the input 174. In this circumstance, the alarm circuit 168 comprises a low blood pressure monitor and does not trip until the blood pressure of the user falls below a predetermined value. It will be further apparent that the comparator 172 may be configured to energize the alarm 180 in the event the signal on the output 118 rises above a predetermined value and in the event it falls below another predetermined value.

Also illustrated in FIG. 3 is a pulse readout circuit 182 for displaying the pulse rate of the user on the array 14. The circuit 182 may be of any suitable type but is illustrated as comprising a lead 184 connected to the output 86 of the amplifier 82, a retriggerable one shot multivibrator 186, a rate multiplier 188 and an output 190 connected to a switch terminal 192 adjacent a switch element 194 on the actuator 32. It will be apparent that the signal on the output 86 carries a train of amplified pulses appearing at a frequency of 0–5 cycles per second indicative of the pulses of the user of the device 10. The multivibrator 186 conditions the signal to the rate multiplier 188 and acts to deliver a single pulse for a short predetermined duration in response to receiving a single pulse. Thus, the multivibrator 186 is triggered by the signal from the peak 78 (FIG. 5) and the delivered pulse from the multivibrator 186 masks the secondary pulses 80. Any suitable multivibrator such as a Model 74121 is operable. The rate multiplier may also be of any suitable type, such as a Model 74167 from Texas Instruments. The rate multiplier 188 basically acts to multiply the number of pulses received from the multivibrator 186 by a constant to produce a number of pulses per minute, corresponding to pulse rate, which is displayed on the array 14 through the switch 28, a lead 196, and the four bit latch 26.

As shown in FIG. 3, the circuit 36 may also comprise a temperature subcircuit 198 for displaying a value representative of body temperature on the array 14. The subcircuit 198 comprises a temperature sensor 200, such as a thermistor, a silicon diode or an integrated circuit such as a National Semiconductor Model 3911, for sensing temperature and delivering a signal proportional thereto on an output 202. The sensor 200 may be located in any convenient site on the underside of the watch casing 12.

The signal on the output 202 is amplified any any suitable amplifier 204 having an output 206 connected to a potentiometer 208. The potentiometer 208, of course, acts to calibrate the voltage appearing on its output 210 which is connected to one or a pair of switch terminals 212, 214. The terminals 212, 214 comprise part of a switch 216 having a switch element 218 normally connecting the output 118 to the converter 136, a switch element 220 normally spaced from the terminals 212, 214 and a switch actuator 222 extending through the watch casing 12 as suggested in FIG. 1. The terminal 214 is connected to the converter 136 by a lead 224. It is accordingly apparent that depressing the switch actuator 222 causes the output 118 to disengage from the converter 136 followed by coupling of the temperature subcircuit 198 to the converter 136. The voltage signal on the output 210 is then converted into a frequency, the magnitude of which is counted by the watch display array 14 following depression of the switch actuator 32.

It is well known that the temperature measured on an individual's body depends to some extent on the location where the temperature is measured. For example, it is well known that oral and rectal temperature readings vary. It will accordingly be apparent that the potentiometer 208 may be adjusted so that the readings visible on the array 14 correspond to a temperature reading taken contemporaneously on the individual.

As shown in FIGS. 2 and 3, the pressure sensor 38 is connected by the lead 62 to a rectifier 226 and battery protection circuit 228 to the battery 34. The rectifier 226 may be of any convenient type and is shown as including a capacitor 230 in series with a first diode 232. The rectifier 226 also comprises a second diode 234 connected at one end between the capacitor 230 and the diode 232 and faces into the input end of the diode 232. The opposite end of the diode 234 is connected to ground 236. A capacitor 238 is connected between the output end of the diode 232 and the ground connection 236. As will be apparent to those skilled in the art, the rectifier 236 comprises a voltage doubler or half wave rectifier and acts to convert an alternating current input into a direct current output.

The protection circuit 228 comprises a diode 240 in series with and facing in the same direction as the diode 232 and a zener diode 242 connected between the output 244 of the diode 240 and a ground connection 246. The diode 240 acts to isolate the battery 34 and prevents battery current from leading off through the capacitor 238 and ground connection 236. The zener diode 242 acts as a device to limit the voltage applied to the battery 34. Consequently, the zener diode 242 is non-conductive until a voltage value in excess of a predetermined level, for example two volts, appears in the output 244 at which time the zener diode 242 conducts and provides a conductive circuit between the output 244 and the ground connection 246 to shunt the excess voltage.

The battery 34 is connected at one end to the ground connection 246 and is connected at the opposite end to a lead 248 having a branch 250 connected to the timing circuit 20 thereby providing power for the timing aspects of the device 10. The lead 248 extends to a switch terminal 252 adjacent a switch element 254 on the actuator 32. Upon depressing the switch actuator 32, the switch element 254 passes into contact with the switch terminal 252 and completes a circuit to a power lead 256 which is connected to the various power inputs of the amplifiers and potentiometers.

It will accordingly be seen that the sensor 38 acts to deliver an electrical signal which is manipulated to provide readouts of the pulse rate of the wearer and/or the blood pressure of the wearer. In addition, the sensor 38 provides an electrical output which is used to energize the display array 14 and/or to charge the battery 34. Accordingly, the expected life of the battery 34 will be substantially increased which is of advantage in itself but which is also of importance in assuring the user that the blood pressure and/or pulse readouts will operate for substantial periods without fear of battery depletion.

Although the invention has been described in its preferred form with a certain degree of particularity, it is understood that the present disclosure of the preferred form is made only by way of example and that numerous changes in the details of construction and the combination and arrangement of parts may be resorted to without departing from the spirit and scope of the invention as hereinafter claimed. It is intended that the patent shall cover, by suitable expression in the appended claims, whatever features of patentable novelty exist in the invention disclosed.

I claim:

1. A body worn body parameter display device comprising a housing having an array for displaying a value of the body parameter and a battery for energizing the array;

means for connecting the battery to the array;

means carried by the housing for sensing a variable body pressure and delivering an electrical signal representative thereof, the sensing means including piezoelectric means having electrical output means;

means operatively connected to the housing for applying the sensing means in data transmitting relation to the body of an individual;

means connecting the electrical output means to the display array for displaying a value responsive to the electrical signal generated by the sensing means; and means for generating and applying electricity to the battery and the array comprising the piezoelectric means and means for connecting the electrical output means to the display array and to the battery.

2. The display device of claim 1 wherein the battery and display array are connected in parallel for simultaneously applying a voltage from the piezoelectric means to the battery and the array.

3. The display device of claim 1 wherein the piezoelectric means comprises a multiplicity of piezoelectric elements connected in series and the electrical output means comprises a plurality of electrical connections, one of the connections communicating between one of the elements and a ground connection and another of the connections communicating between another of the elements and the battery.

4. The display device of claim 1 wherein the housing comprises a timing circuit therein, the applying means comprises a wrist encircling band, and the display array comprises a single digital display array, and the means connecting the electrical output means to the display array for displaying the value comprises switch means for alternatively connecting the timing circuit and the electrical output means to the display array.

5. The display device of claim 1 wherein the electrical signal generated by the sensing means is of alternating current and the means connecting the electrical output means to the display array and the battery includes a rectifier for converting alternating current into direct current and having an output, and means connecting the rectifier output to the display array.

6. The display device of claim 5 further comprising a battery protection circuit between the rectifier and the battery.

7. The display device of claim 6 wherein the battery protection circuit includes a normally non-conductive element in parallel with the battery responsive to a voltage above a predetermined level for shunting the output around the battery upon the occurence of a voltage level in the output above the predetermined level.

8. A wrist watch comprising a housing having therein a timing circuit, a display array in circuit with the timing circuit and a battery in circuit with the timing circuit and the display array for energizing the same;

a pressure sensor carried by the housing for receiving a variable body pressure from a wearer, the pressure sensor including piezoelectric means for delivering an electrical output in response to the variable body pressure and having electrical output means;

means connecting the electrical output means to the display array for displaying a value responsive to the electrical output generated by the piezoelectric means;

means operatively connected to the housing for applying the sensor in pressure transmitting relation to the body of a wearer; and means for generating and applying electricity to the battery and the array comprising the piezoelectric means and means for connecting the electrical output means to the display array and to the battery.

9. The wrist watch of claim 8 wherein the battery and display array are connected in parallel for simultaneously applying a voltage from the piezeoelectric means to the battery and the display array.

* * * * *